United States Patent [19]

Möhring et al.

[11] 4,243,758

[45] Jan. 6, 1981

[54] PROCESS FOR THE PRODUCTION OF REACTION PRODUCTS USING AQUEOUS FORMOSE WHICH HAS BEEN PREPARED WITH THE USE OF A LEAD CATALYST WHICH LEAD CATALYST HAS BEEN REMOVED FROM THE FORMOSE PRODUCT BY CATHODIC ELECTROCHEMICAL DEPOSITION

[75] Inventors: Edgar P. Möhring, Bergisch-Gladbach; Hanns P. Müller, both of Leverkusen, both of Fed. Rep. of Germany

[73] Assignee: Bayer Aktiengesellschaft, Leverkusen, Fed. Rep. of Germany

[21] Appl. No.: 41,263

[22] Filed: May 21, 1979

Related U.S. Application Data

[62] Division of Ser. No. 934,579, Aug. 17, 1978, Pat. No. 4,175,015.

[51] Int. Cl.³ .............................................. C08G 18/14
[52] U.S. Cl. .................................... 521/158; 521/170; 260/29.2 TN; 528/85; 528/272; 528/308; 528/309; 528/405; 568/852; 204/131
[58] Field of Search .................. 260/29.2 TN; 528/85, 528/272, 308, 309, 405; 521/158, 170; 568/852

[56] References Cited

U.S. PATENT DOCUMENTS

| 3,764,499 | 10/1973 | Okubo et al. | 204/149 |
| 3,878,169 | 4/1975 | Guillet et al. | 528/85 |

OTHER PUBLICATIONS

Grant (ed), *Hackh's Chemical Dictionary*, McGraw-Hill, NY, 1944, pp. 352–358.

*Primary Examiner*—Maurice J. Welsh
*Attorney, Agent, or Firm*—Gene Harsh; Joseph C. Gil

[57] ABSTRACT

This invention relates to a continuous or discontinuous process for the removal of catalytic quantities of lead ions from aqueous formose solutions by cationic electro-deposition. The process is preferably carried out with a constant current and in at least three stages, with lower current densities being maintained during the first and last stage than in the middle stages.

4 Claims, No Drawings

PROCESS FOR THE PRODUCTION OF REACTION PRODUCTS USING AQUEOUS FORMOSE WHICH HAS BEEN PREPARED WITH THE USE OF A LEAD CATALYST WHICH LEAD CATALYST HAS BEEN REMOVED FROM THE FORMOSE PRODUCT BY CATHODIC ELECTROCHEMICAL DEPOSITION

This is a division of application Ser. No. 934,579 filed Aug. 17, 1978 now U.S. Pat. No. 4,175,015, issued Nov. 20, 1979.

BACKGROUND OF THE INVENTION

The term "formose" in the context of the present invention means the known mixtures of low molecular weight polyhydroxyl compounds (polyhydric alcohols, hydroxy aldehydes and hydroxy ketones) which are produced by the condensation of formaldehyde hydrate.

The preparation of mixtures of polyhydric alcohols, hydroxy aldehydes and hydroxy ketones by the auto-condensation of formaldehyde hydrate has been described in the literature. Examples, include Butlerow and Loew, Annalen 120, 295 (1861); J.pr. Chem. 33, 321 (1886); Pfeil, chemische Berichte 84, 229 (1951); Pfeil and Schroth, chemische Berichte 85, 303 (1952); R. D. Partridge and A. H. Weiss, Carbohydrate Research 24, 29–44 (1972); the formoses of glyceraldehyde and dihydroxy acetone according to Emil Fischer; German Pat. Nos. 822,385; 830,951 and 884,794; U.S. Pat. Nos. 2,224,910; 2,269,935 and 2,272,378 and British Pat. No. 513,708. These prior art processes have certain disadvantages (poor volume/time yields and colored by-products). New processes have recently been developed by which virtually colorless formoses which are free from undesirable by-products may be prepared in high yields using the conventional catalysts.

According to one of these new processes, the condensation of formaldehyde hydrate is carried out in the presence of catalysts consisting of soluble or insoluble lead (II) salts or of lead (II) ions attached to high molecular weight carriers and in the presence of a co-catalyst consisting of a mixture of hydroxy aldehydes and hydroxy ketones which may be obtained from the condensation of formaldehyde hydrate and which is characterized by the following molar ratios:

Compounds having 3 carbon atoms/compounds having 4 carbon atoms: from 0.5:1 to 2.0:1

Compounds having 4 carbon atoms/compounds having 5 carbon atoms: from 0.2:1 to 2.0:1

Compounds having 5 carbon atoms/compounds having 6 carbon atoms: from 0.5:1 to 5.0:1. The proportion of components having from 3 to 6 carbon atoms is at least 75%, by weight, preferably more than 85%, by weight, based on the total quantity of co-catalyst.

The reaction temperature is generally from 70° to 110° C., preferably from 80° to 100° C. The pH of the reaction solution is adjusted by controlled addition of an inorganic or organic base, first to a value of from 6.0 to 8.0, preferably from 6.5 to 7.0, until from 10 to 60%, preferably from 30 to 50%, of the starting material has been converted. Thereafter the pH is adjusted to a value of from 4.0 to 6.0, preferably from 5.0 to 6.0. It is surprisingly found that the ratios of products in the resulting mixtures of polyols, hydroxy aldehydes and hydroxy ketones may be varied in a reproducible manner by this particular control of the pH followed by cooling at different residual formaldehyde contents (from 0 to 10%, by weight, preferably from 0.5 to 6%, by weight).

The auto-condensation of the formaldehyde hydrate is stopped by cooling and/or by inactivation of the lead-containing catalyst by means of acids. The catalyst is then removed and, if desired, water contained in the products is removed by distillation. Details of this procedure may be found in German Offenlegungsschrift No. 2,639,084.

Another possibility of preparing highly concentrated, colorless formoses in high volume/time yields consists of condensing aqueous formalin solutions and/or paraformaldehyde dispersions in the presence of a soluble or insoluble metal catalyst and in the presence of a co-catalyst which has been prepared by partial oxidation of a dihydric or polyhydric alcohol which has a molecular weight of from 62 to 242 and contains two adjacent hydroxyl groups or a mixture of such alcohols. The pH of the reaction solution is adjusted during condensation by controlled addition of a base. The pH is first maintained at from 6.0 to 9.0 up to from 5 to 40% conversion of the starting material and is thereafter adjusted to from 4.5 to 8.0 until the condensation reaction is stopped. In this second stage, the pH is from 1.0 to 2.0 units lower than in the first reaction phase. The reaction is then stopped at a residual formaldehyde content of from 0 to 10% by weight by inactivation of the catalyst and the catalyst is removed. Details of this process can be found in German Offenlegungsschrift No. 2,718,084.

High quality formoses may also be prepared by the condensation of formaldehyde in the presence of a metal catalyst and more than 10%, by weight, based on the formaldehyde, of one or more dihydric or polyhydric low molecular weight alcohols and/or higher molecular weight polyhydroxyl compounds. Details of this process can be found in German Offenlegungsschrift No. 2,714,104.

It is particularly economical to prepare formose directly from formaldehyde-containing synthesis gases. i.e. without first obtaining aqueous formalin solutions or paraformaldehyde. The synthesis gases obtained from the large scale industrial production of formaldehyde are conducted continuously or discontinuously at temperatures of from 10° to 150° C. into an absorption liquid consisting of water, monohydric or polyhydric low molecular weight alcohols and/or higher molecular weight polyhydroxyl compounds and/or compounds capable of ene-diol formation as co-catalysts and/or, as catalysts, soluble or insoluble metal compounds optionally attached to high molecular weight carriers. The absorption liquid is maintained at a pH of from 3 to 10. The formaldehyde is directly condensed in situ in the absorption liquid (optionally also in a following reaction tube or a following cascade of stirrer vessels). The auto-condensation of formaldehyde is stopped at a residual formaldehyde content of from 0 to 10%, by weight, in the reaction mixture by cooling and/or inactivation of the catalyst with acids. The catalyst is then finally removed. Details of this process can be found in German Offenlegungsschriften Nos. 2,721,093 and 2,721,186.

For most of the processes described above, divalent lead ions are the preferred catalyst. In the presence of compounds of divalent lead the auto-condensation of formaldehyde hydrate will proceed both at a neutral and a slightly acid pH in a high volume/time yield and substantially without undesirable side reactions. For some applications for formose (e.g. when it is to be used as substrate for micro-organisms or before the catalytic hydrogenation to polyhydric alcohols), it is necessary to remove the lead ions present in the products of the process. An obvious method for removal is by chemical precipitation (for example by the addition of sulphuric acid, sodium sulphate, sodium carbonate, sodium sulphide or carbon dioxide gas under pressure). It is found, however, that the hydroxy aldehydes and hydroxy ketones contained in formose have an exceptionally powerful capacity to form complexes with metal ions. In a production setting, removal of lead from aqueous formose solutions by chemical precipitation is too incomplete or is relatively expensive. In addition, formose solutions are difficult to separate from the precipitated lead salts by filtration. Moreover, for economical reasons, the lead salt would have to be converted into a soluble form so that it could be recycled for catalysing the formation of formose. This entails additional expenditure.

Another possibility lies in the removal of lead ions from formose solutions by means of ion exchange resins. The disadvantage of this method, however, is that in practice very large quantities of exchange resin would have to be used. Rinsing and regenerating liquid would also be needed, which would make the removal of the total quantity of lead from formose by means of ion exchange resins technically too complicated and expensive.

DESCRIPTION OF THE INVENTION

It has now surprisingly been found that lead ions may easily be removed from aqueous formose solutions by cationic electrodeposition. This has the advantage that the solution containing lead is not diluted by the removal of lead. Moreover, the deposited lead may subsequently be redissolved in the starting materials for formose synthesis by reversing the polarity of the source of current. It is found that more than 90% of the lead contained in the formose may be deposited in this way within a short time. In view of the great tendency for complex formation between formose and metal ions mentioned above, it was expected that the cationic deposition of lead would be accompanied by high voltage overloads which could lead to undesirable side reactions (deposition of hydrogen, decomposition of formose, oxidation of sugar). It was unexpectedly found that this is not the case.

The present invention thus relates to a process for the removal of lead ions from aqueous formose solutions where the lead is removed by cathodic, electro-chemical deposition.

The aqueous formose solutions obtained from the auto-condensation of formaldehyde hydrate in the presence of compounds of divalent lead as catalysts generally contain about 2500 to 4000 ppm of lead ions. By means of the process according to the present invention, such solutions may be freed from lead down to a final concentration of lead ions of from about 10 to 500 ppm, preferably from 50 to 300 ppm. This residual quantity may then be removed by means of cation exchange resins without great capitol expenditure.

It has been found that electrolytic processes employing a constant voltage at the terminals are not suitable because the current continuously increases during electrolysis as the lead deposits on the cathod. The current density rapidly reaches values which cause vigorous evolution of gas and boiling of the solution. It is therefore preferred to operate at a constant current (isocoulombic deposition).

This is preferably carried out by starting with a current density of from 0.1 to 3, preferably from 0.3 to 1.5, ampere/dm$^2$ at the beginning of electrolysis and keeping the calculated current constant during electrolysis. If the fall in the lead ion concentration of the formose solution is plotted against time at a constant current intensity for various electrolytic experiments, accurate analysis of the graphs obtained shows that it is particularly advantageous to deposit the lead in at least three stages. Relatively low current densities should be used in the first and last stage and relatively high current densities in the middle stage. It is, of course, also possible to incorporate additional intermediate stages.

It is therefore particularly preferred to pass the formose solution which is to be freed from lead through at least three electrolytic cells in succession, employing an initial current density of from 0.1 to 0.7, most preferably from 0.3 to 0.5, ampere/dm$^2$ in the first cell, an initial current density of from 0.8 to 3.0, preferably from 1.0 to 1.5, ampere/dm$^2$ in the second cell, and an initial current density of from 0.2 to 1.0, preferably from 0.3 to 0.8 ampere/dm$^2$, in the third cell. Approximately one third of the total quantity of deposited lead is removed in each cell. Additional cells may also be used. If additional cells are used, the higher current density of the intermediate second cell mentioned above should be used in these additional cells.

Formoses which have been freed from lead by the process according to the present invention may readily be hydrogenated by the conventional methods employed for the hydrogenation of sugars.

Formoses which have been freed from lead according to the present invention and polyhydric alcohols obtained from them by a crossed Cannizzaro reaction or by hydrogenation are valuable starting materials for numerous products which are of considerable interest for practical application.

For example, both the formoses and the reduction products thereof (formites) are very suitable for use as chain-lengthening agents or cross-linking agents in the production of polyurethane resins. Polyisocyanates, low molecular weight polyhydroxyl compounds and optionally higher molecular weight polyhydroxyl compounds, additional chain-lengthening agents, blowing agents, catalysts and other known additives are used to make polyurethanes. High functional polyether polyols may be obtained by the propoxylation and/or epoxylation of formoses or formites. Those polyether polyols having high OH numbers are suitable for the production of rigid or semi-rigid polyurethane foams while those having low OH numbers are suitable for use as starting materials for highly flexible polyurethane foams.

Highly branched polyesters which may be used as additives for alkyd resins to improve their hardness may be synthesized by reacting formose or formite with polybasic carboxylic acids, such as phthalic acid of adipic acid, by the conventional method of polyester condensation. Such polyesters may, of course, also be used as starting components for the production of polyurethane resins.

The lead-free formoses and formites obtained according to the present invention may also be used as moisturizers in cosmetics and synthetic resins and as antifreezes. They may also be used as carbohydrate-containing substrates for the nutrient media of micro-organisms. Products consisting mainly of hydroxy-aldehydes and hydroxy ketones which contain 5 or 6 carbon atoms have proved to be particularly suitable for this purpose.

Owing to their low metal ion content, the formoses which have been treated according to the present invention are also particularly suitable for controlled methylolation reactions with formaldehyde. The formoses are methylolated on the carbon atoms in the α-position to the carbonyl group by an aldol condensation with formaldehyde. For this purpose, aqueous formaldehyde is added to the formoses at a pH of from 8 to 12, preferably from 9 to 11, and the mixture is maintained at from 10° to 100° C., preferably from 30° to 60° C., for a period of from about 10 minutes to 12 hours. Suitable bases for this purpose particularly include tertiary amines, such as triethylamine, tripropylamine or dimethyl benzylamine.

The following Examples serve to illustrate the process of the present invention. The quantities given are parts by weight, or percentages, by weight, unless otherwise indicated.

The fall in lead content with time during the electrolysis of aqueous formose solutions and the change in the specific resistance of the formose solutions with time are given in the Examples. The "simple efficiency" $W_E$ is defined as the quotient of the quantity of lead deposited since the onset of the electrolysis and the quantity which may theoretically be deposited, as calculated from the current consumption. The "differential efficiency" $W_D$ is defined as the quotient of the lead deposited within a given time interval and the quantity of lead which may theoretically be deposited in the same time interval, as calculated from the current consumption.

GENERAL DESCRIPTION OF THE ELECTROLYSIS EXPERIMENT

One liter of a 50% formose solution which has not yet been desalted and has a lead content of 3390 ppm, prepared according to Example 1 of German Offenlegungsschrift No. 2,639,083 is introduced into a chromatographic tank (12×7×19 cm). The solution is slowly stirred using a magnetic stirrer. Carbon plate electrodes each having a surface area of 1.2 dm² are lowered into the solution a distance of 3.9 cm apart and left in the tank for half an hour. A source of current and a voltmeter are connected to the plates with the same direction of polarity as the plates. The solution is then electrolysed at a constant current. At the same time, the voltage across the terminals is recorded at each measuring time point. A sample of the solution is removed every 15 minutes and examined for its residual lead content. Electrolyses were carried out at 7 different current intensities varying from 0.24 to 5.4 amperes.

EXAMPLES

EXAMPLE 1

| Electrolysis at a constant current of 0.24 ampere | | | |
|---|---|---|---|
| Time | | Specific | Efficiency |
| (min) t | Pb Content (ppm) | Resistance (Ω . cm) ζ | Simple $W_E$ / Differential $W_D$ |

| Time (min) t | Pb Content (ppm) | Resistance (Ω . cm) ζ | Simple $W_E$ | Differential $W_D$ |
|---|---|---|---|---|
| 15 | 3165 | 555 | 0.17 | |
| 30 | 3025 | 540 | 0.32 | 0.32 |
| 45 | 2865 | 525 | 0.46 | |
| 60 | 2690 | 512 | 0.56 | 0.77 |
| 75 | 2490 | 505 | 0.63 | |
| 90 | 2290 | 502 | 0.67 | 0.92 |
| 105 | 2100 | 501 | 0.71 | |
| 120 | 1905 | 503 | 0.73 | 0.89 |
| 135 | 1720 | 500 | 0.74 | |
| 150 | 1520 | 500 | 0.765 | 0.89 |
| 165 | 1320 | 500 | 0.77 | |
| 180 | 1135 | 500 | 0.78 | 0.89 |
| 195 | 940 | 500 | 0.785 | |
| 210 | 795 | 501 | 0.775 | 0.78 |
| 225 | 670 | 503 | 0.77 | |
| 240 | 565 | 500 | 0.75 | 0.53 |
| 270 | 420 | 500 | 0.73 | 0.26 |
| 300 | 325 | 500 | 0.69 | 0.21 |

EXAMPLE 2

| Electrolysis at a constant current of 0.36 ampere | | | | |
|---|---|---|---|---|
| Time (min) t | Pb Content (ppm) | Resistance (Ω . cm) ζ | Simple $W_E$ | Differential $W_D$ |
| 15 | 3340 | 525 | 0.09 | |
| 30 | 3230 | 516 | 0.23 | 0.23 |
| 45 | 2960 | 495 | 0.36 | |
| 60 | 2700 | 480 | 0.475 | 0.76 |
| 75 | 2430 | 470 | 0.54 | |
| 90 | 2180 | 455 | 0.58 | 0.74 |
| 105 | 1920 | 449 | 0.61 | |
| 120 | 1660 | 445 | 0.63 | 0.75 |
| 135 | 1400 | 444 | 0.645 | |
| 150 | 1140 | 440 | 0.64 | 0.75 |
| 165 | 960 | 441 | 0.635 | |
| 180 | 720 | 440 | 0.63 | 0.60 |
| 195 | 580 | 440 | 0.62 | |
| 200 | 480 | 439 | 0.595 | 0.35 |
| 225 | 390 | 438 | 0.575 | |
| 240 | 350 | 439 | 0.54 | 0.18 |

EXAMPLE 3

| Electrolysis at a constant current of 0.6 ampere | | | | |
|---|---|---|---|---|
| Time (min) t | Pb Content (ppm) | Resistance (Ω . cm) ζ | Simple $W_E$ | Differential $W_D$ |
| 15 | 3160 | 452 | 0.13 | |
| 30 | 2885 | 430 | 0.30 | 0.30 |
| 45 | 2510 | 412 | 0.415 | |
| 60 | 2215 | 397 | 0.49 | 0.58 |
| 75 | 1840 | 385 | 0.52 | |
| 90 | 1495 | 377 | 0.535 | 0.63 |
| 105 | 1110 | 370 | 0.54 | |
| 120 | 865 | 360 | 0.535 | 0.55 |
| 135 | 660 | 357 | 0.51 | |
| 150 | 555 | 360 | 0.48 | 0.26 |
| 165 | 460 | 359 | 0.45 | |
| 180 | 405 | 358 | 0.43 | 0.13 |
| 195 | 395 | 354 | 0.40 | |
| 210 | 345 | 356 | 0.38 | — |
| 225 | 320 | 355 | 0.36 | |
| 240 | 305 | 355 | 0.335 | — |

EXAMPLE 4

| Electrolysis at a constant current of 1.2 ampere | | | | |
|---|---|---|---|---|
| Time (min) t | Pb Content (ppm) | Resistance (Ω . cm) ζ | Simple $W_E$ | Differential $W_D$ |
| 15 | 3310 | 370 | 0.03 | |
| 30 | 3120 | 355 | 0.10 | 0.10 |

-continued

Electrolysis at a constant current of 1.2 ampere

| Time (min) t | Pb Content (ppm) | Specific Resistance ($\Omega \cdot$ cm) $\zeta$ | Efficiency Simple $W_E$ | Efficiency Differential $W_D$ |
| --- | --- | --- | --- | --- |
| 45  | 2600 | 335 | 0.20  |       |
| 60  | 2100 | 315 | 0.26  | 0.445 |
| 75  | 1600 | 295 | 0.32  |       |
| 90  | 1100 | 275 | 0.33  | 0.44  |
| 105 | 900  | 270 | 0.31  |       |
| 120 | 780  | 270 | 0.28  | 0.14  |
| 135 | 660  | 270 | 0.26  |       |
| 150 | 530  | 270 | 0.24  | 0.11  |
| 165 | 420  | 268 | 0.225 |       |
| 180 | 310  | 266 | 0.22  | 0.095 |
| 195 | 250  | 265 | 0.21  |       |
| 210 | 180  | 265 | 0.20  | 0.06  |
| 225 | 160  | 263 | 0.19  |       |
| 240 | 125  | 263 | 0.18  | 0.02  |

EXAMPLE 5

Electrolysis at a constant current of 1.8 ampere

| Time (min) t | Pb Content (ppm) | Specific Resistance ($\Omega \cdot$ cm) $\zeta$ | Efficiency Simple $W_E$ | Efficiency Differential $W_D$ |
| --- | --- | --- | --- | --- |
| 15  | 3100 | 325 | 0.02  |       |
| 30  | 2765 | 300 | 0.08  | 0.12  |
| 45  | 2220 | 270 | 0.16  |       |
| 60  | 1650 | 245 | 0.205 | 0.33  |
| 75  | 1140 | 230 | 0.21  |       |
| 90  | 765  | 228 | 0.205 | 0.27  |
| 105 | 540  | 228 | 0.20  |       |
| 120 | 420  | 227 | 0.18  | 0.10  |
| 135 | 320  | 226 | 0.165 |       |
| 150 | 240  | 225 | 0.16  | 0.055 |
| 165 | 160  | 225 | 0.15  |       |
| 180 | 100  | 225 | 0.145 | 0.04  |
| 195 | 90   | 224 | 0.14  |       |
| 210 | 80   | 222 | 0.13  | —     |
| 225 | 70   | 220 | 0.125 |       |
| 240 | 60   | 220 | 0.12  | —     |

EXAMPLE 6

Electrolysis at a constant current of 3.6 ampere

| Time (min) t | Pb Content (ppm) | Specific Resistance ($\Omega \cdot$ cm) $\zeta$ | Efficiency Simple $W_E$ | Efficiency Differential $W_D$ |
| --- | --- | --- | --- | --- |
| 15 | 3180 | 300 | 0.02 |      |
| 30 | 2745 | 255 | 0.07 | 0.06 |
| 45 | 1800 | 205 | 0.14 |      |
| 60 | 1065 | 170 | 0.16 | 0.25 |
| 75 | 800  | 150 | 0.15 |      |
| 90 | 520  | —   | 0.12 | 0.08 |

The solution begins to boil after 100 minutes.

EXAMPLE 7

Electrolysis at a constant current of 5.4 ampere

| Time (min) t | Pb Content (ppm) | Specific Resistance ($\Omega \cdot$ cm) $\zeta$ | Efficiency Simple $W_E$ | Efficiency Differential $W_D$ |
| --- | --- | --- | --- | --- |
| 15 | 3000 | 255 | 0.02  | 0.03  |
| 30 | 1930 | 130 | 0.12  | 0.13  |
| 45 | 1170 | —   | 0.13  | 0.135 |
| 60 | 640  | —   | 0.125 | 0.14  |
| 75 | 340  | —   | 0.11  | 0.06  |

The solution begins to boil after 85 minutes.

EXAMPLE 8

This Example demonstrates that the process according to the present invention may be optimized by carrying out the electrolysis in several steps in succession at different constant currents.

Although the efficiency is very high if the process is carried out at a very low constant current (Example 1), electrolysis takes a relatively long time before a desired low residual lead content is obtained. In the procedure according to Example 7, where a high current intensity is maintained, the times required are relatively short, but the efficiency is poor.

The Example described below illustrates the preferred method of carrying out the process. According to this embodiment of the process, electrolysis is carried out at successive currents, each one of which is kept constant for its duration. Three identical apparatus of the type described under "general experimental procedure" are used. Electrolysis in the first apparatus is carried out at the constant current of 0.36 amp, in the second apparatus at 1.2 amp and in the third at 0.6 amp. One liter of the formose solution described in Example 1 is reduced to a lead content of 2200 ppm within 42 minutes in the first apparatus, to 1600 ppm within 21 minutes in the second apparatus and to 500 ppm within 72 minutes in the third apparatus (electrolysis in the third cell could, of course, be continued to a lower lead content, but it was stopped at 500 ppm for the sake of better comparison). It should be noted in this connection that the process of electrolysis could be carried out continuously. In that case, the solution would not be transferred from one apparatus to the next (discontinuously) as in this Example, but would be arranged to flow continuously through cells connected in series. For such a continuous operation, the capacities of the cells and surface areas of the electrodes must be adjusted to the rate of flow. This means that the capacities of the individual cells should be in inverse proportion to the electrolytic current in the cells while the surface areas of the electrodes should be proportional to the currents.

A quantitative comparison between Examples 1, 7 and 8 with regard to the efficiency of lead deposition and the length of electrolysis time required for such deposition shows that the procedure according to Example 8 has been optimized compared with Examples 1 and 7 if one assumes that a procedure may be regarded as optimal when the product of efficiency and speed of deposition at each point in time of electrolysis as represented by the following equation:

$$P = W_D \cdot \frac{\text{quantity deposited}}{\text{time interval}}$$

is maximal. Analysis of the data obtained in Examples 1 to 7 shows that this is the case in Example 8. The total efficiency is also improved in Example 8.

Comparison of total efficiency $$\omega(\omega = \int_0^t W_D \cdot dt)$$

of Examples 1, 7 and 8 and the times of electrolysis required to obtain a residual lead content of 500 ppm are as follows:
for Example 7 and Example 8

$t_7:t_8 = 1:3.2$ $\omega_7:\omega_8 = 1:33$ for Example 1 and Example 8

$t_1:t_8 = 1.8:1$ $\omega_1:\omega_8 = 2.7:1$

It is found, therefore, that the procedure according to Example 8 is 33 times more effective than the procedure according to Example 7 and only about three times slower; compared with Example 1, Example 8 is approximately three times more effective and only about twice as slow.

An even more effective procedure could be obtained by further increasing the number of electrolytic steps, but the cost of the apparatus must be weighed against the process efficiency.

By reversing the polarity of the current after the carbon anode has been replaced by a rod electrode (preferably of silver or copper), the lead deposited on the cathode may be redissolved anodically. This anodic dissolving of lead is preferably carried out in an aqueous formose solution which is later to be used as co-catalyst for the preparation of formose. A lead-containing formose solution having a lead content of 30,000 ppm or more (which is both catalytically and co-catalytically exceptionally efficient) is thereby obtained. Such co-catalyst solutions are particularly preferred for the synthesis of formose because the lead which it contains is in the form of an aqueous formose solution without any complex formation with foreign anions. This is recognized from the deep green to blackish-brown color of such a lead-containing formose solution.

What is claimed is:

1. In a process for the production of polyurethane resins where polyisocyanates are reacted with compounds containing active hydrogen atoms, the improvement which comprises using as the active hydrogen containing compounds aqueous formose which has been prepared with the use of a lead catalyst, which lead catalyst has been removed from the formose product by cathodic electro-chemical deposition.

2. In a process for the production of polyesters comprising reacting a hydroxyl group containing material with a polybasic carboxylic acid, the improvement wherein the hydroxyl group containing material comprises formoses which have been freed from lead by cathodic electro-chemical deposition.

3. In a process for the production of polyether polyols comprising alkoxylation a hydroxyl group containing material the improvement wherein hydroxyl group containing material comprise formoses which have been freed from lead by cathodic electro-chemical deposition.

4. In a process for the methylolation with formaldehyde of carbonyl group containing compounds, the improvement wherein the carbonyl group containing compound comprises formoses which have been freed from lead by cathodic electro-chemical deposition.

* * * * *

UNITED STATES PATENT AND TRADEMARK OFFICE
CERTIFICATE OF CORRECTION

PATENT NO. : 4,243,758
DATED : January 6, 1981
INVENTOR(S) : Edgar P. Möhring and Hanns P. Müller It is certified that error appears in the above-identified patent and that said Letters Patent are hereby corrected as shown below:

On the first page of the patent, Applicant's name is incorrect. The inventors should read Edgar Möhring and Hanns P. Muller.

On the first page of the patent, Applicants' claim for priority should be acknowledged by addition of the following:

[30]  Foreign Application Priority Date
          August 25, 1977 [DE] Federal Republic of Germany
          ...2738274

In Claim 3, line 2, please delete the word "alkoxylation" and insert in its place--alkoxylating--.

In Claim 3, line 3, after the word "wherein" please insert --the--.

Signed and Sealed this

Ninth Day of June 1981

[SEAL]

Attest:

RENE D. TEGTMEYER

*Attesting Officer*      *Acting Commissioner of Patents and Trademarks*